United States Patent [19]

Sawada et al.

[11] Patent Number: 5,292,904
[45] Date of Patent: Mar. 8, 1994

[54] METHOD FOR PRODUCTION OF ETHYLENE OXIDE

[75] Inventors: Masayuki Sawada; Yukihiko Kakimoto, both of Yokohama, Japan

[73] Assignee: Nippon Shokubai Co., Ltd., Osaka, Japan

[21] Appl. No.: 942,632

[22] Filed: Sep. 9, 1992

[30] Foreign Application Priority Data

Sep. 12, 1991 [JP] Japan .................................. 3-233427
Sep. 2, 1992 [JP] Japan .................................. 4-234749

[51] Int. Cl.$^5$ .................... C07D 301/10; C07D 303/04
[52] U.S. Cl. ...................................... 549/534; 422/201
[58] Field of Search ........................................ 549/534

[56] References Cited

U.S. PATENT DOCUMENTS

| | | | |
|---|---|---|---|
| 3,147,084 | 9/1964 | Franzen et al. | 23/288 |
| 4,061,659 | 12/1977 | Nielsen et al. | 549/534 |
| 4,847,393 | 7/1989 | Langley | 549/534 |
| 4,882,444 | 11/1989 | Dobson et al. | 549/534 |

FOREIGN PATENT DOCUMENTS

| | | | |
|---|---|---|---|
| 130807 | 1/1985 | European Pat. Off. | 549/534 |
| 1499285 | 8/1966 | France . | |
| 3810631 | 8/1964 | Japan . | |
| 32408 | 3/1979 | Japan | 549/534 |
| 156070 | 11/1989 | Japan . | |
| 1134318 | 11/1968 | United Kingdom . | |
| 1449091 | 9/1976 | United Kingdom . | |
| 1449092 | 9/1976 | United Kingdom . | |

OTHER PUBLICATIONS

European Search Report, EP 92 30 8245, Jan. 4, 1993.
Annex of JP 3-233427, 1991, Japan.

*Primary Examiner*—Joseph E. Evans
*Attorney, Agent, or Firm*—Omri M. Behr; Matthew J. McDonald

[57] ABSTRACT

The production of ethylene oxide by the catalytic vapor phase oxidation of ethylene with a molecular oxygen-containing gas is effected in a reactor provided with a preheating zone, a reaction zone, a cooling zone, a partition plate separating the first two portions from the third portion, and a multiplicity of reaction tubes piercing the two separated sections by a method which comprises supplying hot water to the cooling zone of the reactor, forwarding zone of the hot water discharged from the cooling zone to a gas-liquid separation tank, circulating the remainer of the hot water in conjunction with the cooling hot water to the cooling zone, supplying the hot water separated in the gas-liquid separation tank to the reaction zone to remove the heat of the oxidation reaction, and circulating the hot water extracted in the form of a gas-liquid mixed phase to the gas-liquid separation tank. The method is excellent to prevent isomerization of ethylene oxide to acetaldelyde which is impurity, excels in thermal efficiency and exhibits ideal durability of the partition plate.

4 Claims, 2 Drawing Sheets

METHOD FOR PRODUCTION OF ETHYLENE OXIDE

BACKGROUND OF THE INVENTION

1. Field of the Invention

This invention relates to a method for the production of ethylene oxide. More particularly, it relates to a method for producing ethylene oxide by the catalytic vapor phase oxidation of ethylene with a molecular oxygen-containing gas, which method is characterized by the use of hot water as a heat medium for the reaction apparatus.

2. Description of the Prior Art

In the process for catalytic vapor phase oxidation of a hydrocarbon, specifically the catalytic vapor phase oxidation of ethylene with a molecular oxygen-containing gas in the presence of a silver catalyst for the production of ethylene oxide, the catalytic vapor phase reaction is carried out by mixing a hydrocarbon-containing gas containing saturated hydrocarbons such as methane and ethane, nitrogen, carbon dioxide, argon, and oxygen in addition to ethylene with a molecular oxygen-containing gas such as air, oxygen-enriched air, or pure oxygen in a prescribed ratio and introducing the resultant mixed gas into a reactor packed with a silver catalyst. Like virtually all hydrocarbons, ethylene reacted with molecular oxygen in the presence of a silver catalyst induces exothermic reactions represented by the following formulas:

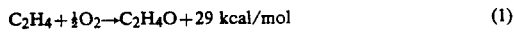

$$C_2H_4 + \tfrac{1}{2}O_2 \rightarrow C_2H_4O + 29 \text{ kcal/mol} \quad (1)$$

$$C_2H_4 + 3O_2 \rightarrow 2CO_2 + 2H_2O \; 316 \text{ kcal/mol} \quad (2)$$

For the purpose of enhancing the yield of ethylene oxide, these exothermic reactions ought to be controlled so as to allow the reaction of Formula (1) to proceed in a large ratio. In this connection, studies are being pursued regarding silver catalyst and reaction method. By the existing technical standard, however, the simultaneous occurrence of the reaction of Formula (2), namely the complete oxidation of ethylene which entails evolution of a large amount of heat of reaction, cannot be avoided.

Besides Formulas (1) and (2) mentioned above, there exists another formula which affects the yield of ethylene oxide. It is the isomerization of the produced ethylene oxide into acetaldehyde which proceeds as indicated by Formula (3) shown below.

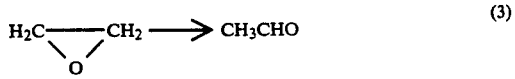

$$H_2C\!\!-\!\!\!-\!\!\!-\!\!CH_2 \longrightarrow CH_3CHO \quad (3)$$
$$\diagdown \!\! O \!\! \diagup$$

No matter how high the selectivity in the conversion of ethylene to ethylene oxide may be, the degradation of the yield of ethylene oxide inevitably ensues when the isomerization of the produced ethylene oxide into acetaldehyde notably occurs.

Acetaldehyde has a boiling point very close to that of ethylene oxide. Therefore, isolation of ethylene oxide from acetaldehyde by such a process as distillation, calls for a large amount of energy even when the acetaldehyde is contained in an extremely small amount. Further, since the number of trays in the distillation column is large and the reflux ratio therein is high and consequently the cost of equipment is high, an increase in the acetaldehyde content affects the cost of purification to a large extent.

The reactor outlet gas has a high temperature and, therefore, is made to exchange heat with the reactor inlet gas for recovery of heat. The cooled reaction product gas gives rise to a drain which mainly contains water, ethylene oxide, and acetaldehyde. Since this drain has a high acetaldehyde content, the isolation of ethylene oxide from the drain is extremely difficult to perform. The drain, therefore, leads to a decline in the yield of ethylene oxide.

The cooled reaction product gas is introduced into an absorption column and absorbed therein by an absorption liquid mainly containing water and ethylene glycol and the absorption liquid now containing the absorbed reaction product gas is forwarded to the next step for purification. In this case, ethylene oxide and water partly react in the absorption liquid to form ethylene glycols. For the purpose of maintaining the concentration in the system, the absorption liquid containing the ethylene glycols is partly removed from the system and subjected to purification and recovery of ethylene glycols. Due to the impurities originating in the aldehyde contained in the absorption liquid, the recovered ethylene glycols have degraded qualities, particularly in uv absorbance. Even for the purpose of preventing the decrease of qualities, the content of these aldehydes in the absorption liquid is preferably low.

Minimization of the isomerization of ethylene oxide into acetaldehyde, therefore, constitutes in itself one of the major tasks assigned to the production of ethylene oxide.

Since the demand for ethylene oxide has been growing in recent years and for the purpose of lowering the cost of production of ethylene oxide, plans for enlarging the existing plants for the production of ethylene oxide are gaining in impetus. Thus, the amount of the heat of reaction produced in the reactors per ethylene oxide production plant is large as plainly surmised from the aforementioned formulas of reaction, though the enhancement of yield has been achieved to a considerable extent. The question on how the large amount of the heat of reaction ought to be safely and effectively recovered for reuse poses a problem of safety and economy for the production of ethylene oxide by the catalytic vapor phase oxidation of ethylene with molecular oxygen.

Generally, in the catalytic vapor phase oxidation of a hydrocarbon with molecular oxygen, the method of passing the reaction product gas through a cooling zone filled with a packing for the purpose of curbing secondary reactions has been known to the art JP-B-39-17,254(1964). The practice of applying this method to the production of ethylene oxide by the catalytic vapor phase oxidation of ethylene with molecular oxygen has also been known to the art. GB-1,449,091 and GB-1,449,092, for example, teach a method which comprises causing the reaction product obtained in a reaction zone to be passed through a cooling zone which adjoins or does not adjoin the reaction zone and contains or does not contain an inert packing. U.S. Pat. No. 4,061,659 discloses a method which comprises passing the reaction product through a cooling zone packed with inert refractory particles having a surface area of not more than 1 m²/g.

The reaction apparatuses which are used for these methods adopt a procedure which comprises circulating a high boiling heat medium such as Dowtherm (a proprietary product of the Dow Chemical Company) or a low boiling heat medium such as water to the reaction zone for removal of heat and using a high boiling heat medium such as Dowtherm in the cooling zone. These methods have the disadvantage in that the thermal media are high boiling dangerous substances which are difficult to handle and the apparatuses are complicated and not easy to operate.

Heretofore, as a reactor for the production of ethylene oxide by the catalytic vapor phase oxidation of ethylene with molecular oxygen, a shell-and-tube exchanger type reactor which is so constructed as to cool the reaction tubes of the reactor by forcibly circulating with a pump a high boiling heat medium such as Dowtherm between the exteriors of the reaction tubes and a heat exchanger adapted to form steam thereby removing the heat of reaction, cause the heat medium consequently heated to an elevated temperature to give the heat thereof to the water through the heat exchanger and make the water generate steam, and recirculating the consequently cooled heat medium and cooling the exteriors of the reaction tubes again has been known to the art.

Besides, a shell-and-tube exchanger type reactor which is so constructed as to effect formation of steam directly on the shell side of the reactor when a vaporizable heat medium such as water is used and, therefore, obviate the necessity for using a heat exchanger adapted to form steam as described above and permit spontaneous circulation when hot water is used and, therefore, obviate the necessity for installing a pump has been known to the art.

JP-B-1-56,070(1989) proposes a method for the catalytic vapor phase oxidation of ethylene, which uses a shell-and-tube exchanger type reactor having a reaction zone and a cooling zone adjoining each other and effects the oxidation by first supplying hot water to the cooling zone, cooling the reaction product gas cooling zone, causing the hot water to be further heated and discharged out of the reactor, flushing the hot water thereby inducing gas-liquid separation, then supplying the hot water to the reaction region thereby removing the heat of reaction by cooling, allowing the hot water to boil and depart from the reactor, flushing the hot water for gas-liquid separation, circulating the hot water to the reaction zone, recovering the steam, and accomplishing effective recovery of heat.

In these conventional reactors for the production of ethylene oxide, however, the effect of curbing the occurrence of aldehydes cannot be amply fulfilled because the hot water of a temperature in the range between 100° C. and 150° C. is first passed through the cooling zone provided for a vertical shell-and-tube exchanger type reactor and then used for cooling the reaction zone and, as a natural consequence, the amount of the hot water passed through the cooling zone is very small as compared with that passed through the reaction zone and the reactor is destined to be cooled unevenly. Moreover, the baffle plate portion of the cooling zone, the lower tube plate contiguous to the hot water in the cooling zone, and the lower tube plate contiguous to the reaction product gas have the possibility of generating thermal stress and causing vibration.

This invention has been produced to solve the problems encountered by the conventional reactors as described above.

An object of this invention is to provide a method for the production of ethylene oxide which eliminates the possibility of the baffle plate portion of the cooling zone of the vertical shell-and-tube exchanger type reactor for the production of ethylene oxide, the lower tube plate contiguous to the hot water of the cooling zone, and the lower tube plate contiguous to the reaction product gas generating thermal stress and inciting vibration, promotes enhancement of thermal efficiency, and heightens the effect of curbing the isomerization of ethylene oxide into aldehydes as impurities.

SUMMARY OF THE INVENTION

To be specific, this invention relates to a method for the production of ethylene oxide by the catalytic vapor phase oxidation of ethylene with a molecular oxygen-containing gas, which method is characterized by using a vertical shell-and-tube exchange type reactor provided with a shell, an upper tube plate, a lower tube plate, a partition plate separating the shell side of a reaction zone and the shell side of a cooling zone, and a multiplicity of reaction tubes and the preheating zone having the inlet of the reaction tubes packed with an inert packing, the reaction zone having the reaction tubes packed with a silver catalyst between the inlet and outlet thereof, and the cooling zone having the outlet of the reaction tubes packed with an inert packing and effecting the production by supplying hot water at a temperature in the range between 100° C. and 150° C. through a first hot water supplying conduit to the cooling zone of the reactor and allowing this hot water to contact the outer sides of the reaction tubes, passing the reaction product gas of a temperature in the range between 200° C. and 300° C. in the cooling zone, forwarding the hot water having exchanged heat with the reaction product gas containing ethylene, ethylene oxide, and oxygen and consequently acquired an elevated temperature in the range between 200° C. and 250° C. through a first hot water discharge conduit to a gas-liquid separation tank and circulating the remainder of the hot water to the cooling zone by means of a pump, introducing the hot water separated in the gas-liquid separation tank via a second hot water supplying conduit into the reaction zone and allowing the introduced hot water to contact the outer sides of the reaction tubes of the reaction zone to remove the heat of reaction, bringing the hot water boiled in the reaction zone and consequently made to assume the form of a gas-liquid mixed phase into contact with the outer sides of the reaction tubes of the preheating zone thereby preheating the raw material gas, and inducing spontaneous circulation of the preheated raw material gas via a second hot water discharge conduit into the gas-liquid separation tank.

This invention uses the hot water departing from the cooling zone of the reactor as a recycle to the cooling zone and, therefore, has the effect of precluding the baffle portion of the cooling zone of the vertical shell-and-tube exchange type reactor for the production of ethylene oxide, the lower tube plate contiguous to the hot water of the cooling zone, and the lower tube plate contiguous to the reaction product gas from generating thermal stress and inducing vibration and, at the same time, enhancing the thermal efficiency compared to a conventional method wherein hot water departing from the cooling zone of the reactor is not recycled to the cooling zone. Further, since the temperature distribution in the outlet gas from the cooling zone is dispersed only sparingly, this invention has an effect of curbing the isomerization of the produced ethylene oxide into acetaldehyde and attaining enhancement of the yield of ethylene oxide.

Owing to the use of hot water as a heat medium for the reaction apparatus, the possibility of the reaction apparatus catching fire is nil. The use of hot water allows spontaneous circulation of the heat medium and obviates the necessity for installing a circulation pump in the reaction zone. As a result, the harmful influences of the abnormal elevation of the temperature of the reaction zone which would be caused by a sudden stop of the circulation pump in the reaction zone operated for other heat medium than the hot water are absent. Further, the use of the hot water brings about the advantage that the removal of heat is carried out with high efficiency and consequently the conversion of the reaction is higher than when other heat medium is used because hot water enjoys high thermal conductivity.

This invention, by causing the reaction product gas flowing out of the reaction zone and containing ethylene and oxygen to be cooled in the cooling zone to a temperature in the range between 150° C. and 250° C., is able to repress the temperature of the raw material gas to a level in the range between 100° C. and 200° C. in the heat exchanger, which serves the purpose of preheating the raw material gas with the reaction product gas and consequently increasing the oxygen concentration in the raw material gas. Further, owing to the use of the reaction apparatus of this invention, the hot water which is supplied as the heat medium is allowed to generate steam directly on the shell side of the reactor and the steam so generated is recovered in an amount proportional to the amount of the hot water supplied to the reaction apparatus. The fact that the hot water departing from the cooling zone is used for replenishing the cooling medium of the reaction zone is advantageous from the standpoint of utility of thermal energy and economy of construction and equipment.

As already point out, the method of using hot water as a cooling medium through a cooling zone and re-supplying a reaction zone has been known to the art and produces the same effect in terms of construction and equipment cost.

The method of this invention, however, is excellent in prevention of isomerization of ethylene oxide to acetaldehyde, and differs in respect of purification cost of ethylene oxide, quality of the ethylene glycols recovered from a reaction gas absorption column and increase in the yield of ethylene oxide.

DESCRIPTION OF THE PREFERRED EMBODIMENT

Figure 1:
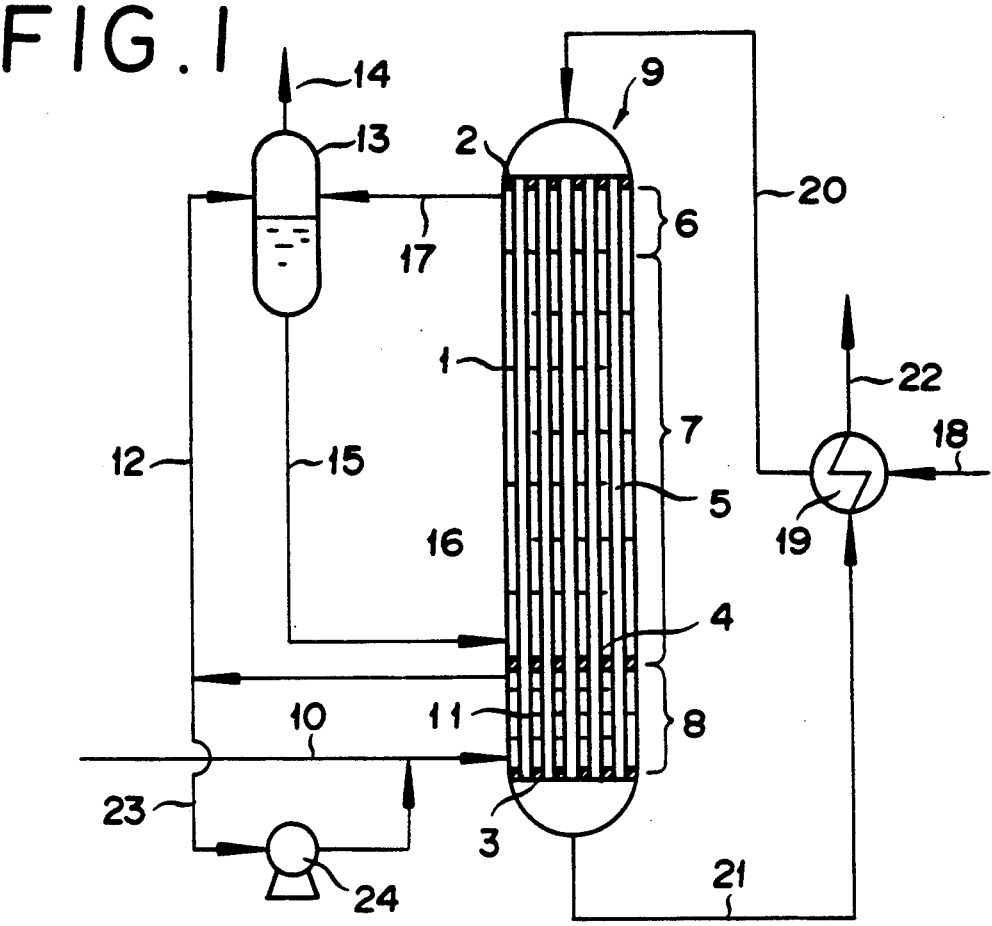
FIG. 1 is an explanatory diagram illustrating a method for the production of ethylene oxide.

In the reaction apparatus of this invention, the preheating zone is the region in which the inlet of the reaction tubes are packed with an inert packing, the reaction zone is the region in which the reaction tubes are packed with a silver catalyst between the inlet and outlet thereof, and the cooling zone is the region in which the outlet parts of the reaction tubes are packed with an inert packing.

The inert packing to pack the preheating zone and the cooling zone of the reactor of this invention is only required to be an inert refractory substance. It may be in the form of spheres, hemispheres, pellets, rings, and amorphous particles, for example. The inert refractory substances which are preferably usable for the inert packing include alumina, silica-alumina, zirconia, magnesia, and silicon carbide, for example, which are generally used as carriers for a silver catalyst. Particularly, stainless steel, alpha-alumina, and zirconia are preferable examples. The shape, size, pores, specific surface area, apparent porosity, etc. of the inert refractory packing may be suitably selected in consideration of the pressure drop and mechanical strength of the packing to be manifest when the carrier is packed into the reaction tubes. The inert packing may be spheres or rings having an average diameter generally in the range between 1/16 and ½ inch, preferably between 3/16 and ⅓ inch. An inert refractory packing having precipitated therein at least one element selected from among sodium, potassium, rubidium, cesium, lithium, strontium, barium, and thallium, preferably from among sodium, potassium, rubidium, cesium, and thallium, is used advantageously. This inert refractory packing may be particularly used in packing the reaction tubes of the cooling zone.

The process and reaction conditions under which the method of this invention can be embodied may be any of those process and reaction conditions which have been heretofore known in the art. As processes for producing ethylene oxide by the catalytic vapor phase oxidation of ethylene with molecular oxygen, for example, the air oxidation method using air as an oxygen source and the oxygen oxidation method using pure oxygen are available. The method of this invention can be effectively applied to either of these processes. Particularly, the oxygen oxidation method which allows the amount of reaction per passage through the catalyst bed to be increased and enables the ethylene oxide concentration to be heightened can be adopted effectively.

In respect of the operating conditions, the raw material gas is a mixture of ethylene, oxygen, carbon dioxide, nitrogen, argon, methane, ethane, and a reaction inhibitor such as 1,2,dichloroethane etc. Though it is preferable that the ethylene concentration in the raw material gas as high as possible, it is generally not more than 40% by volume, particularly in the range between 15 and 35% by volume. The carbon dioxide gas concentration is not more than 10% by volume, particularly in the range between 4 and 8% by volume. When the raw material gas contains methane or ethane, the methane functions to shift the range of explosion towards the safe side and narrow the range of explosion. Thus for the sake of the reaction, it is desirable to contain methane or ethane as a diluent for the reaction gas in the highest allowable concentration.

The reaction pressure is generally in the range between 0 and 40 kg/cm$^2$·G, preferably in the range between 10 and 30 kg/cm$^2$·G. The reaction temperature is generally in the range between 150° C. and 300° C., preferably in the range between 180° C. and 280° C. The space velocity is generally in the range between 1000 and 10000 hr$^{-1}$, preferably in the range between 2000 and 8000 hr$^{-1}$.

The catalyst for packing the reaction zone may be any of the silver catalysts heretofore known to the art. An inert refractory carrier having a specific surface area not more than 20 m$^2$/g, preferably in the range between 0.01 and 10 m$^2$/g and an apparent porosity not less than 20% by volume, preferably in the range between 30 and 70% by volume, and having a minute amount of metallic silver precipitated thereon is preferably used. It is preferable to incorporate therein as a reaction promoter at least one element selected from among alkali metals, alkaline earth metals, thallium, antimony, and tin. The carrier materials which are effectively usable herein include such inert refractory substances as, for example, alumina, silica-alumina, silicon carbide, zirconia, and magnesia. Particularly, an inert refractory carrier having alpha-alumina as a main component thereof is preferably used. The carrierparticles may be in the form of spheres, hemispheres, rings, and pellets. They are particularly preferable in the form of spheres or rings. The carrier particles have an average diameter generally in the range between 1/16 and ¼ inch, preferably in the range between 3/16 and 5/16 inch. Economically, it is preferably that the amount of silver to be deposited is preferable to be in the range between 1 and 20% by weight, preferably in the range between 5 and 15% by weight, based on the amount of the catalyst.

Now, this invention will be described more specifically below with reference to the accompanying drawings. The drawings represent preferred embodiments of the catalytic vapor phase oxidation of ethylene with a molecular oxygen-containing gas in the presence of a silver catalyst and an example of the apparatus used for the oxidation, which are illustrative and not limitative of this invention.

In FIG. 1, a vertical shell-and-tube exchanger type reactor 9 comprising a shell 1, an upper tube plate 2, a lower tube plate 3, a partition plate 4 separating a shell side 16 of a reaction zone 7 and a shell side 11 of a cooling zone 8, and a multiplicity of reaction tubes 5 is provided with a preheating zone 6 and having an inlet of the reaction tubes 5 packed with an inert packing, the reaction zone 7 having the reaction tubes 5 packed with a silver catalyst between the inlet and outlet thereof, and the cooling zone 8 having the outlet of the reaction tubes 5 packed with an inert packing. Hot water of a temperature in the range between 100° C. and 150° C., preferably between 110° C. and 140° C., is supplied through a first hot water supply conduit 10 to the cooling zone 8 and allowed to contact the exteriors of the reaction tubes 5 passing the reaction product gas of a temperature in the range between 200° C. and 300° C., preferably between 220° C. and 280° C. in the cooling zone. The hot water which has exchanged heat with the reaction product gas containing ethylene, ethylene oxide, and oxygen and has consequently acquired an elevated temperature in the range between 200° C. and 250° C., preferably between 210° C. and 240° C. is forwarded through a first hot water discharge conduit 12 to a gas-liquid separation tank 13. The remainder of this hot water is passed through a hot water circulation conduit 23 and then supplied by a hot water circulation pump 24 through the first hot water supply conduit 10 to the shell side 11 of the cooling zone 8. The weight ratio of the hot water forwarded to the gas-liquid separation tank 13 to the hot water circulated to the cooling zone 8 is in the range between 1:0.5 to 1:5, preferably between 1:1 to 1:3.

The hot water which has been forwarded through the first hot water discharge conduit 12 to the gas-liquid separation tank 13 in flushed in the gas-liquid separation tank 13. The steam resulting from the separation is discharged out of the system via a conduit 14 and recovered and the hot water is supplied through a second hot water supply conduit 15 to the reaction zone 7 and brought into contact with the exteriors of the reaction tubes 5.

The hot water which, on contact with the exteriors of the reaction tubes 5 of the reaction zone 7, has absorbed the heat of reaction and consequently boiled in the reaction zone 7 and assumed the form of a gas-liquid mixed phase, contacts the exteriors of the reaction tubes 5 of the preheating zone 6 and consequently preheats the raw material gas. The hot water is then circulated spontaneously through a second hot water discharge conduit 17 to the gas-liquid separation tank 13 and flushed therein. The steam which has been separated in the gas-liquid separation tank 13 and has acquired a temperature in the range between 210° C. and 280° C., preferably between 220° C. and 250° C. and a pressure in the range between 19 and 64 kg/cm$^2$·G, preferably between 23 and 40 kg/cm$^2$·G can be recovered via the conduit 14.

In the meantime, the raw material gas containing ethylene and a molecular oxygen-containing gas and having a temperature in the range between 30° C. and 80° C. is introduced through a conduit 18, passed through a heat exchanger 19 and consequently preheated to a temperature in the range between 100° C. and 200° C., preferably between 150° C. and 190° C., and introduced through a raw material gas supply conduit 20 into the reaction tubes 5 of the vertical shell-and-tube exchanger type reactor 9. The reaction product gas which has flowed through the preheating zone 6, the reaction zone 7, and the cooling zone 8 and consequently acquired a temperature in the range between 150° C. and 250° C., preferably between 180° C. and 240° C., is forwarded to the heat exchanger 19 and used therein to preheat the raw material gas. The reaction production gas which has been used for preheating the raw material gas is forwarded through a conduit 22 to an absorption column.

The reaction product gas containing ethylene oxide is led to the absorption column and brought into counterflow contact with the absorption liquid formed mainly of water and consequently recovered in the form of an aqueous ethylene oxide solution. Then, the aqueous ethylene oxide solution is forwarded to a stripper and whereby ethylene oxide is stripped by applying heat to the bottom zone of the stripper. The aqueous solution which now contains substantially no ethylene oxide is recovered from the bottom of the stripper and used as the absorption liquid in the absorption column. The stripped solution which contains ethylene oxide, water, carbon dioxide gas, inert gases (nitrogen, argon, methane, and ethane), and such low boiling impurities as formaldehyde and such high boiling impurities as acetaldehyde and acetic acid, departs from the top of the stripper and is supplied to a dehydration tower. By heating the bottom of the dehydration column, water containing no ethylene oxide is extracted from the bottom of the dehydration tower. The vapor from the top of the dehydration column is condensed. The condensate is forwarded to a light ends column. By heating the bottom of the light ends column, such volatile fractions as formaldehyde are separated through the top of the light ends column. The bottoms of the lightends column are supplied to an ethylene oxide distillation column and subjected therein to final separation from acetaldehyde to obtain an ethylene oxide fraction. The separation of ethylene oxide and acetaldehyde from each other is difficult. Thus, the operating conditions of the ethylene oxide distillation column are varied largely by the amount of acetaldehyde contained in the reaction product gas.

When the aldehyde concentration in the aqueous ethylene oxide solution emanating from the ethylene oxide absorption column is 50 ppm, for example, the acetaldehyde concentration in the ethylene oxide fraction obtained from the ethylene oxide distillation column is 15 ppm. When the aldehyde concentration in the aqueous ethylene oxide solution emanating from the ethylene oxide absorption column is 100 ppm, the acetaldehyde concentration in the ethylene oxide fraction obtained from the ethylene oxide distillation oxide operated under the same conditions is 23 ppm.

The following measures are conceivable as means for decreasing the acetaldehyde concentration in the ethylene oxide fraction from 23 ppm to 15 ppm.

(1) To increase the number of trays in the distillation column to 8.

(2) To increase the reflux ratio to distillation column to about two times.

The measure of (1) entails a problem of increasing the cost of construction of the distillation column. The measure of (2) suffers from a problem of entailing an addition to the energy spent for heating the distillation column. In either case, the amount of acetaldehyde to be extracted from the bottom is increased and consequently the loss of ethylene oxide is increased and the productivity is lowered.

This invention has the effect of precluding the baffle portion of the cooling zone of the vertical shell-and-tube exchanger type reactor for the production of ethylene oxide, the lower tube plate contiguous to the hot water of the cooling zone, and the lower tube plate contiguous to the reaction product gas from generating thermal stress and inducing vibration, promoting improvement of the thermal efficiency, and enhancing repression of the isomerization of ethylene oxide into acetaldehyde as an impurity.

In the vertical shell-and-tube exchanger type reactor for use in this invention comprising the shell plate 1, the upper tube plate 2, the lower tube plate 3, the partition plate 4 for separating the shell side 16 of the reaction zone and the shell side 11 of the cooling zone 8, and the multiplicity of reaction tubes 5 is provided with the preheating zone 6 having the inlet of the reaction tubes 5 packed with an inert packing, the reaction zone 7 having the reaction tubes 5 packed with a silver catalyst between the inlet and the outlet thereof, and the cooling zone 8 having the outlet of the reaction tubes 5 packed with an inert packing, the removal of the heat of reaction can be uniformly effected, the reaction tubes of the vertical shell-and-tube exchanger type reactor for the production of ethylene oxide can be prevented from generating thermal stress and inducing vibration, the thermal efficiency can be improved, and the formation of aldehydes in the reaction product gas can be curbed by supplying the hot water of a temperature in the range between 100° C. and 150° C. through the first hot water supply conduit 10 to the cooling zone 8 and bringing the introduced hot water into contact with the exteriors of the reaction tubes 5 passing the reaction product gas at a temperature in the range between 200° C. and 300° C. in the cooling zone 8, forwarding the hot water having exchanged heat with the reaction product gas containing ethylene, ethylene oxide, and oxygen and consequently assumed a temperature in the range between 200° C. and 250° C. through the first hot water discharge conduit 12 to the gas-liquid separation tank 13, recycling the remainder of the hot water by the pump 24 through the conduit 23 to the shell side 11 of the cooling zone 8, introducing the hot water separated in the gas-liquid separation column 13 through the second hot water supply conduit 15 to the shell side 16 of the reaction zone 7 and bringing the introduced hot water into contact with the exteriors of the reaction tubes 5 of the reaction zone 7, forwarding the hot water having removed the heat of reaction, boiled in the reaction zone 7, and assumed the form of a gas-liquid mixed phase into contact with the exteriors of the reaction tube 5 of the preheating zone 6 thereby preheating the raw material gas, and allowing the hot water to be spontaneously circulated through the second hot water discharge conduit 17 to the gas-liquid separation tank 13.

The reaction product gas flowing out of the catalyst bed, containing ethylene, ethylene oxide, and oxygen, and having an elevated temperature in the range between 200° C. and 300° C. is cooled in the cooling zone packed with an inert packing by supplying the hot water of a temperature in the range between 100° C. and 150° C. to the shell side of the cooling zone. Thus, the temperature of the reaction product gas at the outlet of the cooling zone can be controlled to a level in the range between 150° C. and 250° C. In the production of ethylene oxide by the catalytic vapor phase oxidation of ethylene with molecular oxygen, for example, this oxidation is carried out at a temperature between 200° C. and 300° C. and the reaction product gas naturally assumes roughly the same temperature and consequently induces the isomerization of ethylene oxide into acetaldehyde. The cooling zone which is installed immediately next to the reaction zone which is discharging the reaction product gas, therefore, has the effect of repressing the isomerization of ethylene oxide into acetaldehyde.

In the conventional operation, the reaction product gas flowing out of the outlet of the reaction zone and containing ethylene, ethylene oxide, and oxygen has an elevated temperature and the exchange of heat performed between the raw material gas and the reaction product gas in the heat exchanger elevates the temperature of the raw material gas, with the result that the interiors of the tubes leading to the inlet of the reactor are retained at an elevated temperature.

Thus, the conventional operation has entailed the disadvantage that the oxygen concentration in the raw material gas must be repressed to a low level thereby sacrificing productivity for the purpose of keeping the oxygen concentration below the lower limit of the range of explosion at the prevalent temperature. The method of this invention has the function of not only decreasing the possibility of explosion of the hot reaction product gas flowing out of the catalyst bed and containing ethylene, ethylene oxide, and oxygen but also allowing an increase in the oxygen concentration in the reaction product gas or the raw material gas and promising an improvement in the productivity.

Now, this invention will be described more specifically below with reference to working examples, which are purely illustrative and not limiting on the scope of this invention.

EXAMPLE 1

In a vertical shell-and-tube exchanger type reactor 9 provided, as illustrated in FIG. 1, comprising a shell plate 1, an upper tube plate 2, a lower tube plate 3, a partition plate 4 for separating a shell side 16 of a reaction zone 7 and a shell side 11 of a cooling zone 8, and 13 reaction tubes 5 and having the inlet of the packing tubes 5 packed with an inert refractory alumina packing, the reaction zone 7 having the reaction tubes 5 packed with a silver catalyst between the inlet and outlet thereof, and the cooling zone 8 having the outlet of the reaction tubes 5 packed with a cesium-deposited inert refractory alumina packing, hot water at a temperature of 130° C. and hot water at a temperature of 220° C. supplied through a conduit 23 were supplied at respective flow rates of 90 kg/hr and 170 kg/hr through a first hot water supply conduit 10 to the shell side 11 of the cooling zone 8. The hot water which has cooled the exteriors of the reaction tubes 5 of the cooling zone passing the reaction product gas emanating from the reaction tubes 5 of the reaction zone 7, having a temperature of 255° C., and containing ethylene, ethylene oxide, and oxygen, absorbed the heat of reaction, and assumed an elevated temperature of 240° C. was partly forwarded at a flow rate of 90 kg/hr through a first hot water discharge conduit 12 to a gas-liquid separation tank 13. The remainder was passed through a hot water circulating conduit 23 and supplied by a hot water circulating pump 24 at a flow rate of 170 kg/hr through the first hot water supply conduit to the shell side 11 of the cooling zone 8.

The hot water on the shell side 11 at this time had a Reynolds number of 3100. The hot water of a temperature of 240° C. flowing out of the bottom of the gas-liquid separation tank 13 was forwarded at a flow rate of 4500 kg/hr through a second hot water supply conduit 15 to the shell side 16 of the reaction zone 7.

The steam which had contacted the exteriors of the reaction tubes 5 of the reaction zone 7 and the preheating zone 6 in the boiling state of a gas-liquid mixed phase, induced spontaneous circulation in a path leading from a second hot water discharge conduit 17 to the gas-liquid separation tank 13, and isolated in the gas-liquid separation tank 13 and consequently allowed to assume a pressure of 33.1 kg/cm$^2$·G and a temperature of 240° C. was passed at a flow rate of 90 kg/hr through a conduit 14 and recovered.

In the meantime, a raw material gas containing 20% by volume of ethylene, 8% by volume of molecular oxygen, and 6% by volume of carbon dioxide and having a temperature of 45° C. was introduced through a raw material gas supply conduit 18 to the shell side of a heat exchanger 19 and made to exchange heat with the reaction product gas of a temperature of 210° C. introduced through a reaction product gas discharge conduit 21 to the tubes side of the heat exchanger 19. The reaction product gas consequently cooled to 75° C. was forwarded through a conduit 22 to the ethylene oxide absorption column and brought into counterflow contact with an absorption liquid formed mainly of water to effect recovery of an aqueous ethylene oxide solution. The composition of this solution was as shown in Table 2.

Figure 2:
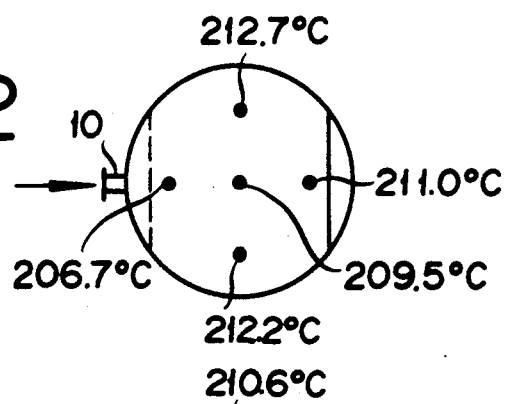
FIG. 2 is a diagram showing temperature distribution in outlet gas from the cooling zone shown in FIG. 1 as obtained in Example 1.

The raw material gas preheated to 180° C. was passed through a raw material supply conduit 20 and introduced at a space velocity of 5000 hr$^{-1}$ into the reaction tubes 5 of the vertical shell-and-tube exchanger type reactor 9. The reaction product gas which had gone through the preheating zone 6, the reaction zone 7, and the cooling zone 8 was forwarded through a reaction gas discharge conduit 21 to the heat exchanger 19. The temperature distribution in the outlet gas of the cooling zone 8 was as shown in FIG. 2. The acetaldehyde concentration of the outlet gas of the reactor in the conduit 21 was as shown in Table 1.

When the reactor was opened and inspected after one year's continued operation, deformation was not found on the outer surfaces of the tubes on the shell side 11 of the cooling zone 8 or on the inner structures such as the baffle in the vertical shell-and-tube exchanger type reactor 9 for the production of ethylene oxide.

CONTROL 1

Figure 4:
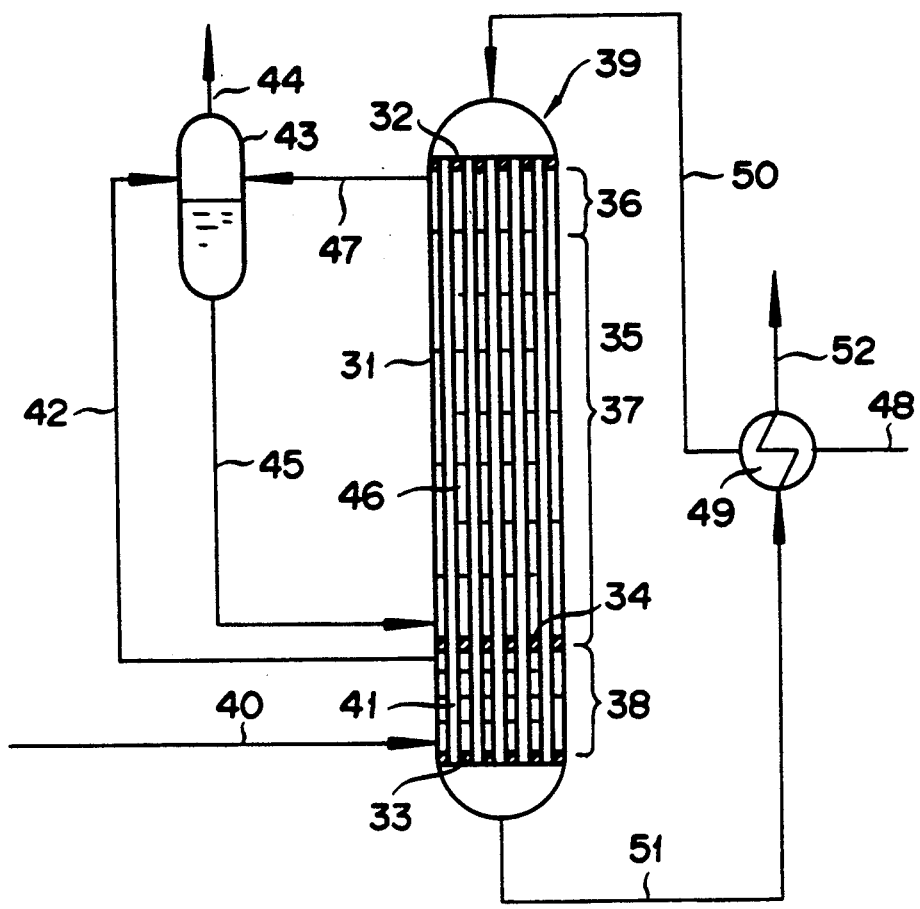
FIG. 4 is an explanatory diagram illustrating a conventional method for the production of ethylene oxide.

In a vertical shell-and-tube exchanger type reactor 39 which was provided, as illustrated in FIG. 4, comprising a shell plate 31, an upper tube plate 32, a lower tube plate 33, a partition plate 34 for separating a shell side 46 of a reaction zone 37 and a shell side 41 of a cooling zone 38, and 13 reaction tubes 35 and a preheating zone 36 having the inlet of the reaction tubes 35 packed with an inert refractory alumina, a reaction zone 37 having the reaction tubes 35 packed with a silver catalyst between the inlet and outlet thereof, and a cooling zone 38 having the outlet of the reaction zone 35 packed with a cesium-deposited inert refractory alumina, hot water of a temperature of 130° C. was supplied at a flow rate of 90 kg/hr through a first hot water conduit 40 to a shell side 41 of the cooling zone 38. The hot water which had cooled the exteriors of the reaction tubes 35 of the cooling zone 38 passing the reaction product gas emanating from the reaction tubes 35 of the reaction zone 37, having a temperature of 255° C., and containing ethylene, ethylene oxide, oxygen, and carbon dioxide gas, absorbed the heat of reaction, and assumed an elevated temperature of 240° C. was forwarded in zone at a flow rate of 90 kg/hr through a first hot water discharge conduit 42 to a gas-liquid separation tank 43. The hot water on the shell side 41 at this time had a Reynolds number of 1000.

The hot water of a temperature of 240° C. emanating from the bottom of the gas-liquid separation tank 43 was introduced at a feed rate of 4500 kg/hr through a second hot water supply conduit 45 to a shell side 46 of the reaction zone.

The steam which had contacted the exteriors of the reaction tubes 35 of the reaction zone 37 and the preheating zone 36 in the boiling state of a gas-liquid mixed phase, induced spontaneous circulation through a path leading from a second hot water discharge conduit 47 to the gas-liquid separation tank 43, isolated in the gas-liquid separation tank 43, and made to assume a pressure of 33.1 kg/cm$^2$·G and a temperature of 240° C. was recovered at a flow rate of 90 kg/hr via a conduit 44.

Figure 5:
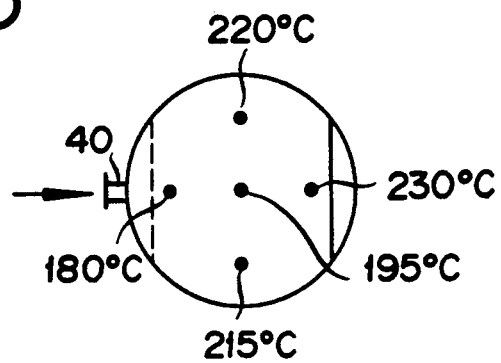
FIG. 5 is a diagram showing temperature distribution in outlet gas from the cooling zone shown in FIG. 4 as obtained in Control 1.

In the meantime, a raw material gas containing 20% by volume of ethylene, 8% by volume of molecular oxygen, and 6% by volume of carbon dioxide and having a temperature of 45° C. was introduced through a conduit 48 to the shell side of a heat exchanger 49. The reaction product gas which had been made to exchange heat with the reaction product gas of a temperature of 210° C. introduced through the reaction product gas discharge conduit 51 to the tubes side of the heat exchanger 49 and consequently had been cooled to 75° C. was forwarded through a conduit 52 to the ethylene oxide absorption column and brought into counterflow contact with an absorption liquid formed mainly of water, to effect recovery of an aqueous ethylene oxide solution. The composition of this solution was as shown in Table 2. In the meantime, the raw material gas which had been preheated to 180° C. was introduced at a space velocity of 5000 hr$^{-1}$ through a raw material gas supply conduit 50 to the reaction tubes 35 in the vertical shell-and-tube exchanger type reactor 39. The reaction product gas which had gone through the preheating zone 36, the reaction zone 37, and the cooling zone 38 was forwarded through a reaction product gas discharge conduit 51 to the heat exchanger 49. The temperature distribution in the outlet gas of the cooling zone 38 was as shown in FIG. 5. The acetaldehyde concentration in the outlet gas of the reaction zone in the conduit 51 was as shown in Table 1.

When the reactor was opened and inspected after one year's continued operation, slight signs of deformation were found on the outer surfaces of the reaction tubes on the shell side 41 of the cooling zone 38 and in the inner structures such as the baffle in the vertical shell-and-tube exchanger type reactor for the production of ethylene oxide.

EXAMPLE 2

In an apparatus of identical structure with the apparatus of Example 1, except that the number of reaction tubes was increased to 3064, hot water at a temperature of 130° C. and hot water of a temperature of 220° C. mixed and supplied through a conduit 23 were supplied at respective feed rates of 23 t/hr and 35 t/hr through a first hot water supply conduit 10 to a shell side 11 of a cooling zone 8 of a vertical shell-and-tube exchanger type reactor 9. The hot water which had cooled the exteriors of reaction tubes 5 of the cooling zone 8 passing the reaction product gas emanating from the reaction tubes 5 of a reaction zone 7, having a temperature of 255° C., and containing ethylene, ethylene oxide, oxygen, and carbon dioxide gas, absorbed the heat of reaction, and allowed to assume an elevated temperature of 240° C. was partly forwarded at a flow rate of 23 t/hr through a first hot water discharge conduit 12 to a gas-liquid separation tank 13. The remainder of the hot water was passed through a hot water circulating conduit 23 and supplyed by a hot water circulating pump 24 at a flow rate of 35 t/hr through the first hot water supply conduit 10 to the shell side 11 of the cooling zone 8.

The hot water on the shell side 11 at this time had a Reynolds number of 64000. The hot water at a temperature of 240° C. flowing out of the bottom of the gas-liquid separation tank 13 was introduced at a flow rate of 1350 t/hr through a second hot water supply conduit 15 to the shell side 16 of the reaction zone 7. The steam at a pressure of 33.1 kg/cm$^2$·G and a temperature of 240° C isolated in the gas-liquid separation tank 13 was recovered at a rate of 23 t/hr via a conduit 14.

Figure 3:
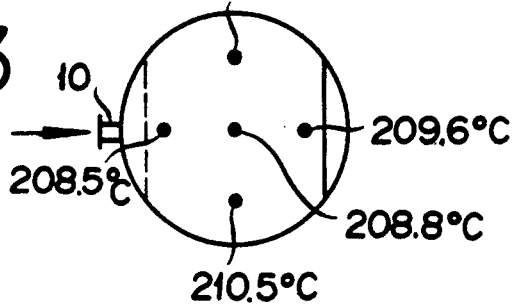
FIG. 3 is a diagram showing temperature distribution in outlet gas from the cooling zone shown in FIG. 1 as obtained in Example 2.

In the meantime, the raw material gas was introduced at a space velocity of 5000 hr$^{-1}$ through a raw material gas supply conduit 20 into the reaction tubes 5 of the vertical shell-and-tube exchanger type reactor 9. The temperature distribution in the outlet gas of the cooling zone 8 was as shown in FIG. 3. The aldehyde concentration in the outlet gas of the reactor was as shown in Table 1. This gas was brought into counterflow contact with an absorption liquid formed mainly of water, to effect recovery of an aqueous ethylene oxide solution. The composition of this solution was as shown in Table 2.

When the reactor was opened and inspected after one year's continued operation, deformation was not found on the outer surfaces of the reaction tubes on the shell side 11 of the cooling zone 8 or in the inner structures such as the baffle in the vertical shell-and-tube exchanger type reactor for the production of ethylene oxide.

TABLE 1

| | Reaction product gas | | |
|---|---|---|---|
| | Example 1 Conduit 21 | Control 1 Conduit 51 | Example 2 Conduit 21 |
| acetaldehyde (ppm) | 2.0 | 4.0 | 2.4 |

TABLE 2

| | Example 1 | Control 1 | Example 2 |
|---|---|---|---|
| ethylene oxide (wt %) | 3.5 | 3.5 | 3.2 |
| glycols (wt %) | 8.3 | 8.3 | 8.4 |
| water (wt %) | 88.2 | 88.2 | 89.4 |
| acetaldehyde (ppm) | 59 | 115 | 65 |

What is claimed is:

1. A method for the production of ethylene oxide by the catalytic vapor phase oxidation of ethylene with a molecular oxygen-containing gas, which method is characterized by using a vertical shell-and-tube exchanger type reactor comprising a shell plate, an upper tube plate, a lower tube plate, a partition plate for separating a shell side of a reaction zone and a shell side of a cooling zone, and a multiplicity of reaction tubes and a preheating zone having the inlet of the reaction tubes packed with an inert packing, a reaction zone having the reaction tubes packed with a silver catalyst between the inlet and the outlet thereof, and a cooling zone having the outlet of the reaction tubes packed with an inert packing and effecting the production by supplying hot water at a temperature in the range between 100° C. and 150° C. through a first hot water supply conduit to the cooling zone, where said hot water contacts the exteriors of said reaction tubes containing a reaction product gas at a temperature in the range between 200° C. and 300° C. in said cooling zone, and exchanges heat with the reaction product gas containing ethylene, ethylene oxide, and oxygen, and assumes a temperature in the range between 200° C. and 250° C. causing a first portion of said hot water to be forwarded through a first hot water discharge conduit to a gas-liquid separation tank, circulating the remainder of said hot water by a pump to said cooling part, introducing the hot water separated in said gas-liquid separation tank through a second hot water supply conduit to said reaction zone, allowing the introduced hot water to contact the outer sides of the reaction tubes of the reaction zone to remove the heat of the reaction, and bringing into contact with the exteriors of said reaction tubes in said preheating zone the remainder portion of hot water which has contacted the exteriors of said reaction tubes in said reaction zone, absorbed the heat of reaction, and assumed the boiled state of a gas-liquid mixed phase in said reaction zone thereby preheating raw material gas and inducing spontaneous circulation of said gas-liquid mixed phase through a second hot water discharge conduit to said gas-liquid separation tank.

2. A method according to claim 1, wherein of the hot water discharged from said cooling zone, the portion forwarded to said gas-liquid separation tank and the portion circulated to said cooling zone are in such proportions that the weight ratio thereof is in the range between 1:0.5 and 1:5.

3. A method according to claim 1, wherein of the hot water discharged from said cooling zone, the portion forwarded to said gas-liquid separation tank and the portion circulated to said cooling zone are in such proportions that the weight ratio thereof is in the range between 1:1 and 1:3.

4. A method according to claim 2, wherein the temperature of said hot water which has exchanged heat with said reaction product gas is in the range between 220° C. and 280° C.

* * * * *